United States Patent [19]

Schaper et al.

[11] Patent Number: 4,661,286

[45] Date of Patent: Apr. 28, 1987

[54] OXASPIRODODECANE DERIVATIVES AND PERFUME COMPOSITIONS CONTAINING THEM

[75] Inventors: Ulf A. Schaper, Krefeld; Siegfried Blöesl, Düsseldorf; Klaus Bruns, Krefeld-Taar, all of Fed. Rep. of Germany

[73] Assignee: Henkel Kommanditgesellschaft auf Aktien, Duesseldorf, Fed. Rep. of Germany

[21] Appl. No.: 844,231

[22] Filed: Mar. 24, 1986

Related U.S. Application Data

[63] Continuation of Ser. No. 576,184, Feb. 2, 1984.

[30] Foreign Application Priority Data

Feb. 26, 1983 [DE] Fed. Rep. of Germany ....... 3306798

[51] Int. Cl.$^4$ ..................... A61K 7/46; C07D 307/93
[52] U.S. Cl. ................................. 252/522 R; 549/311
[58] Field of Search ..................... 252/522 R; 549/311

[56] References Cited

U.S. PATENT DOCUMENTS

| | | | |
|---|---|---|---|
| 4,009,127 | 2/1977 | Ohloff et al. | 252/522 |
| 4,010,286 | 3/1977 | Hall et al. | 252/522 R |
| 4,174,327 | 11/1979 | Renold et al. | 549/331 |
| 4,192,782 | 3/1980 | Hall et al. | 549/331 X |
| 4,252,693 | 2/1981 | Schulte-Elte et al. | 549/331 X |
| 4,336,197 | 6/1982 | Fankhauser | 549/331 |

FOREIGN PATENT DOCUMENTS 3306789 8/1984 Fed. Rep. of Germany .

OTHER PUBLICATIONS

Hall et al., CA 92:169065K (1980).
The Chemical Abstracts, Registry Handbook Registry No. 6 2079-29-2.
Advanced Organic Chemistry, by Fieser and Fieser, p. 585.

Primary Examiner—Anton H. Sutto
Attorney, Agent, or Firm—Ernest G. Szoke; Henry E. Millson, Jr.; Mark A. Greenfield

[57] ABSTRACT

This invention is directed to oxaspirododecane derivatives, the preparation thereof, and perfume compositions containing same.

20 Claims, No Drawings

OXASPIRODODECANE DERIVATIVES AND PERFUME COMPOSITIONS CONTAINING THEM

This application is a continuation of application Ser. No. 576,184, filed Feb. 2, 1984.

FIELD OF THE INVENTION

This invention is directed to bicyclic compounds. More particularly, this invention is directed to oxaspirododecane derivatives, the preparation thereof, and novel perfume compositions containing same.

BACKGROUND OF THE INVENTION

Due to the varying availability of many natural perfume components and the need to adapt to changing fashions in taste, the perfume industry has a constant need for new perfumes which, either on their own or in the form of compositions, represent valuable perfumes with interesting fragrance notes. Since the specific synthesis of perfumes of the desired olfactory quality is not possible because the connections between structure and perfume properties are not very well known, there is a continuing need to find compounds which exhibit valuable perfume properties.

OBJECTS OF THE INVENTION

It is an object of the invention to provide perfuming agents and perfume compositions having characteristic fragrances and excellent adherence.

It is also an object of this invention to provide perfuming agents and perfume compositions comprising oxaspirododecane derivatives.

It is a further object of this invention to provide oxaspirododecane derivatives.

These and other objects of the invention will become more apparent in the discussion below.

DETAILED DESCRIPTION OF THE INVENTION

It has been found that 1-oxa-spiro-[4,7]-dodecanes of the formulas

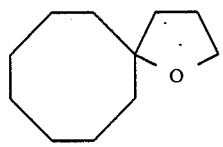

(I)

and

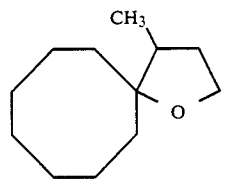

(II)

constitute valuable new perfuming agents. These compounds are readily volatile and, accordingly, have particularly intense fragrance notes and lasting fragrances of high quality.

The olfactory properties of the compound of Formula I, with a civet, skatole, indole note, are particularly interesting. However, the compound of Formula II, which has an earthy, technical, indole-like note, may also be advantageously used for certain perfume compositions.

The compound of Formula I represents a hitherto unknown compound. The compound may be produced by method steps known from the literature in the following manner:

The first reaction step comprises the radical addition of acrylic acid with cyclooctanol, which reaction is initiated by di-tert.butyl peroxide. The hydroxy acid formed as intermediate immediately cyclizes under the reaction conditions to form a lactone (III). This proceeds as shown in the following reaction scheme:

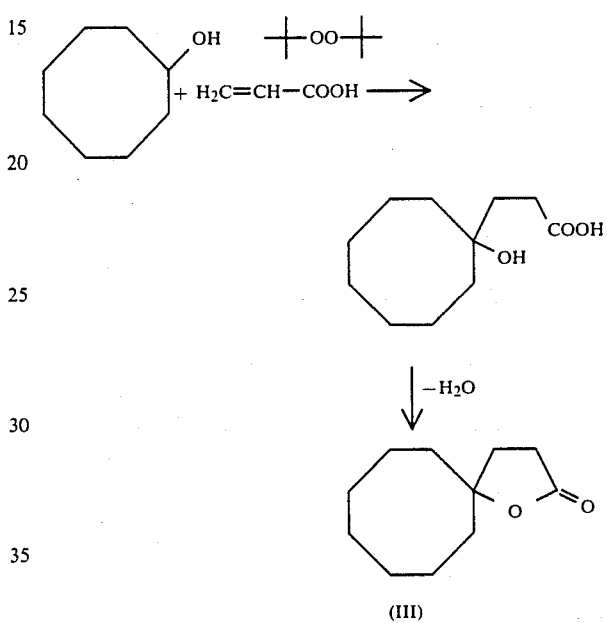

(III)

To avoid rapid polymerization of the acrylic acid, the reaction has to be carried out in dulute solution, i.e., it is best to use a 5 to 20 molar excess of the cyclooctanol. Thereafter, the lactone (III) is reduced with a complex metal hydride, such as LiAlH$_4$, for example, to form the diol (IV) in a very high yield, as shown in the following reaction scheme:

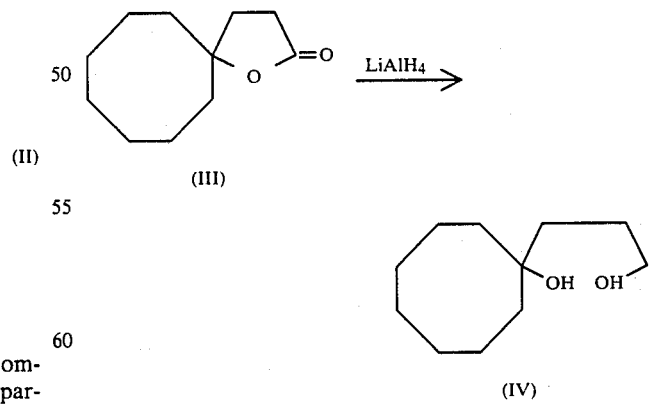

The diol (IV) is not isolated. In the third process step, cyclization to form the 1-oxa-spiro-[4,7]-dodecane of Formula I according to the invention is carried out by azeotropically distilling off the water with toluene. The catalyst used is p-toluenesulfonic acid in a quantity of approximately 10% by weight based upon the weight of the diol (III), because the unsaturated alcohol is preferentially formed if smaller quantities are used. This step proceeds as follows:

$$\text{(IV)} \xrightarrow[H_2O]{p\text{-}Ts} \text{(I)}$$

The compound of Formula II is prepared in similar fashion, with the exception that crotonic acid is used in place of acrylic acid in the first step.

The compounds of Formulas I and II can be mixed with other perfumes in various quantitative proportions to form new perfume compositions. In general, a compound of Formula I or II, or a mixture thereof, in the perfume composition will comprise from about 1 to 50 percent by weight, based upon the total weight of the perfuming composition. The remainder of the composition is comprised of conventional perfumery constituents. Perfume compositions of this type can be used directly as a perfume in extract perfumery, or, alternatively, for perfuming cosmetics, such as creams, lotions, toilet waters, aerosols, shampoos, both preparations, or soaps, or for perfuming technical articles, such as detergents, cleansers, softeners, disinfectants, fabric treatment preparations, and the like. For the perfuming of the various products, the perfume compositions are generally added to these products in concentrations of from about 0.05 to 2 percent by weight, based upon the weight of the finished product.

The following examples are intended to illustrate the invention and are not to be construed as limiting.

EXAMPLES

PREPARATION OF LACTONES OF FORMULA III

Example 1

Three mols of cyclooctanol and 0.045 mol of di-tert-.butyl peroxide were initially introduced into a reaction vessel and heated to 150° C. Then, 0.3 mol of acrylic acid was dissolved in 1 mol of cyclooctanol, and the resulting solution was added dropwise with stirring over a period of from 3 to 10 hours. After cooling, 200 ml of ether were added to the reaction mixture, which was then treated with iron-(II) sulfate to destroy the peroxides, washed first with soda solution and then with water until neutral reaction was obtained, dried over sodium sulfate, and concentrated. The excess starting alcohol was distilled off, and the product was subjected to fractional distillation in an oil pump vacuum.

Yield: 32.7 gm of 1-oxa-spiro-[4,7]-dodecan-2-one
B.p.$_{0.07}$: 86° C.
$^1$H—NMR (CDL$_3$) $\delta$=2.58 ppm (2H, t), 1.7 ppm (16H, m).
$n_D^{20}$: 1.4949

Example 2

The procedure of Example 1 was repeated, with the exception that crotonic acid was used in place of acrylic acid.

Yield: 20.6 gm of 1-oxa-4-methyl-spiro-[4,7]-dodecane-2-one
B.p.$_{0.02}$: 105° C.
$^1$H-NMR (CDCL$_3$) $\delta$=1.9 ppm (17H, m), 1.03 ppm (3H, d).

PREPARATION OF COMPOUNDS OF FORMULAS I AND II

Example 3

A quantity of 1.1 mols of LiAlH$_4$ was introduced under dry nitrogen into 150 ml of ether. One mol of lactone from Example 1, dissolved in 150 ml of ether, was slowly added dropwise with stirring, followed by stirring for another hour. Then, 220 ml of water were slowly added dropwise with cooling, and the reaction mixture was acidified with 10% sulfuric acid. The organic phase was separated off and washed with saturated sodium chloride solution. The ether was distilled off, and the residue was taken up in toluene.

After addition of 17 gm of p-toluenesulfonic acid, the mixture was heated to boiling temperature, and the water of reaction formed was azeotropically distilled off. The toluene solution was washed until neutral and concentrated, and the spiroether was subjected to fractional distillation.

Yield: 90.7 gm of 1-oxa-spiro-[4,7]-dodecane
B.p.$_{16}$: 103° C.
$^1$H—NMR (CDCl$_3$) $\delta$=3.72 ppm (2H, t), =1.80 ppm (18H, m).
$n_D^{20}$: 1.4828
Odor: Civet, skatole, indole note.

Example 4

The procedure of Example 3 was repeated, with the exception that the lactone of Example 2 was used in place of the lactone of Example 1.

Yield: 91.2 gm of 1-oxa-4-methyl-spiro-[4,7]-dodecane
B.p.$_{20}$: 115° C.
$^1$H—NMR (CDCl$_3$) $\delta$=3.72 ppm (2H, t), =1.84ppm (17H, m), =1.0 ppm (3H, d).
Odor: earthy, technical, indole note.

PERFUME COMPOSITION

Example 5

Chypre Formulation

| Component | Parts by Weight |
|---|---|
| 1-Oxa-spiro-[4,7]-dodecane (FORMULA I) | 300 |
| Galaxolide | 300 |
| "AMBROXAN"(; available from Henkel KGaA), 10% in isopropyl myristate | 300 |
| Bergamot oil | 50 |
| Rose oil bulgar | 30 |
| Carrot seed oil | 20 |
| Celery seed oil | 10 |
| α-Methyl ionone | 10 |
| Vetiver oil | 10 |
| Jasmine absolue | 10 |
| "ARTRINON"(; available from Henkel KGaA) | 10 |
| Sandalwood oil | 5 |
| Moschus ketone | 3 |
| Orange oil (terpene-free) | 5 |
| Oakmoss absolue | 3 |
| Undecylene aldehyde (10% in diethyl phthalate) | 3 |
| Cyclopentadecanolide | 2 |
| Angelica root oil | 1 |
| Phenyl ethyl alcohol | 28 |

| Component | Parts by Weight |
|---|---|
| | 1000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

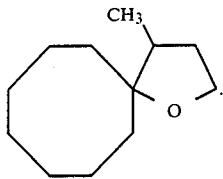

(I)

2. A perfume composition comprising a perfume-effective amount of the compound of claim 1 in admixture with at least one customary perfume composition constituent.

3. A perfume composition comprising a perfume-effective amount of a compound of the formula

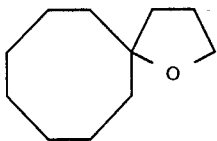

(II)

in admixture with at least one customary perfume composition constituent.

4. The perfume composition of claim 2 wherein said compound is present in about 1-50% by weight, based upon the total weight of said composition.

5. The perfume composition of claim 3 wherein said compound is present in about 1-50% by weight, based upon the total weight of said composition.

6. The perfume composition of claim 2 wherein said constituent comprises at least one other perfume.

7. The perfume composition of claim 3 wherein said constituent comprises at least one other perfume.

8. The perfume composition of claim 4 wherein said constituent comprises at least one other perfume.

9. The perfume composition of claim 5 wherein said constituent comprises at least one other perfume.

10. A method for imparting a desired aroma to a product comprising adding thereto an aroma-effective amount of the perfume composition of claim 2.

11. A method for imparting a desired aroma to a product comprising adding thereto an aroma-effective amount of the perfume composition of claim 3.

12. A method for imparting a desired aroma to a product comprising adding thereto an aroma-effective amount of the perfume composition of claim 4.

13. A method for imparting a desired aroma to a product comprising adding thereto an aroma-effective amount of the perfume composition of claim 5.

14. A method for imparting a desired aroma to a product comprising adding thereto an aroma-effective amount of the perfume composition of claim 6.

15. A method for imparting a desired aroma to a product comprising adding thereto an aroma-effective amount of the perfume composition of claim 7.

16. A method for imparting a desired aroma to a product comprising adding thereto an aroma-effective amount of the perfume composition of claim 8.

17. A method for imparting a desired aroma to a product comprising adding thereto an aroma-effective amount of the perfume composition of claim 9.

18. A method for imparting a desired aroma to a product comprising adding thereto about 0.05-2% by weight of the perfume composition of claim 2, based upon the total weight of said product.

19. A method for imparting a desired aroma to a product comprising adding thereto about 0.05-2% by weight of the perfume composition of claim 3, based upon the total weight of said product.

20. A method for imparting a desired aroma to a product comprising adding thereto about 0.05-2% by weight of the perfume composition of claim 4, based upon the total weight of said product.

* * * * *